US008579899B2

(12) United States Patent
Ahmadi (10) Patent No.: US 8,579,899 B2
(45) Date of Patent: Nov. 12, 2013

(54) BONE FIXATION SYSTEM

(75) Inventor: Shahryer Ahmadi, Rochester, MN (US)

(73) Assignees: Emil Schemitsch, Thornhill, Ontario (CA); Shahryar Ahmadi, Rochester, MN (US)

( * ) Notice: Subject to any disclaimer, the term of this patent is extended or adjusted under 35 U.S.C. 154(b) by 159 days.

(21) Appl. No.: 12/972,016

(22) Filed: Dec. 17, 2010

(65) Prior Publication Data

US 2011/0152864 A1 Jun. 23, 2011

(30) Foreign Application Priority Data

Dec. 18, 2009 (CA) .................................... 2688903

(51) Int. Cl.
*A61B 17/56* (2006.01)
*A61B 17/58* (2006.01)
*A61B 17/80* (2006.01)
*A61F 2/30* (2006.01)

(52) U.S. Cl.
USPC ................................ 606/71; 606/280; 606/70

(58) Field of Classification Search
USPC .......................... 606/280–299, 70, 71, 62–68; 623/21.11–21.19
See application file for complete search history.

(56) References Cited

U.S. PATENT DOCUMENTS

| | | | |
|---|---|---|---|
| 2,496,126 A | 1/1950 | Haboush | |
| 3,561,437 A | 2/1971 | Orlich et al. | |
| 3,782,374 A | 1/1974 | Fischer | |
| 4,973,332 A * | 11/1990 | Kummer | 606/65 |
| 4,988,350 A | 1/1991 | Herzberg | |
| 5,190,544 A | 3/1993 | Chapman et al. | |
| 5,300,074 A | 4/1994 | Frigg | |
| 5,462,547 A * | 10/1995 | Weigum | 606/65 |
| 5,591,168 A | 1/1997 | Judet et al. | |
| 5,749,872 A | 5/1998 | Kyle et al. | |
| 6,110,175 A | 8/2000 | Scholl | |
| 7,033,377 B2 * | 4/2006 | Miller, III | 606/213 |
| 7,316,687 B2 | 1/2008 | Aikins et al. | |
| 2006/0004361 A1 | 1/2006 | Hayeck et al. | |
| 2006/0122606 A1 * | 6/2006 | Wolgen | 606/71 |
| 2006/0235401 A1 * | 10/2006 | Baldwin et al. | 606/69 |
| 2008/0027458 A1 * | 1/2008 | Aikins et al. | 606/96 |
| 2009/0299369 A1 * | 12/2009 | Orbay et al. | 606/70 |

OTHER PUBLICATIONS

Technique Guide: 4.5 mm 90 Degrees Cannulated LC-Angled Blade Plate Instrument and Implant Sets, Stainless Steel and Titanium, Synthes (USA) 1998.

* cited by examiner

*Primary Examiner* — Kevin T Truong
*Assistant Examiner* — Si Ming Lee
(74) *Attorney, Agent, or Firm* — Philip C. Mendes da Costa; Bereskin & Parr LLP/S.E.N.C.R.L., s.r.l.

(57) ABSTRACT

A bone fixation system has a first fixation device. The first fixation device has a first longitudinally extending bone insertion blade having an orienting portion, and a first plate extending transversely from the first bone insertion blade and positionable along a surface of a bone. The bone fixation system further has a second fixation device. The second fixation device has second longitudinally extending bone insertion blade orientatively interactive with the orienting portion, and a second plate extending transversely from the second bone insertion blade and positionable along the surface of the bone adjacent the first plate. When assembled, the second bone insertion blade has an orientation that is based on an orientation of the orienting portion.

17 Claims, 6 Drawing Sheets

FIG 2

BONE FIXATION SYSTEM

FIELD

The disclosure relates to a bone fixation system. Specifically, the disclosure relates to a bone fixation system suitable for use in repairing broken bones, such as a break near or in the trochanter of the femur. The disclosure also relates to a method for using such a system.

INTRODUCTION

The following is not an admission that anything discussed below is prior art or part of the common general knowledge of persons skilled in the art.

U.S. Pat. No. 7,316,687 (Aikins et al.) discloses a blade plate, as well as instruments and methods for securing the blade plate to a bone to reduce a bone fracture. The blade plate includes a plate portion and a blade portion extending at an angle relative to the plate portion. The plate portion includes a plurality of holes for receipt of bone screws for securing the blade plate to the bone. A strut screw, inserted through a hole in the plate portion, spans the angle between the plate and blade portions, and threadingly engages a hole in the blade portion to slightly draw the plate and blade portions together to compress and support the bone fracture. A pair of top screws is inserted through holes in the plate portion at angles with respect to the strut screw on either side of the strut screw. Additionally, the blade plate is designed to closely conform to the surface of the bone to minimize the gap between the bone and the blade plate. In order to secure the blade plate to a bone, a chisel/drill guide, chisel, insertion guide, and screw drill guides are provided.

SUMMARY

The following summary is provided to introduce the reader to the more detailed discussion to follow. The summary is not intended to limit or define the claims.

The bone fixation system utilizes a two-part system. In accordance with one aspect of this system, a first bone fixation device is utilized to orient a second bone fixation device. Each of the first and second bone fixation devices may be generally L-shaped with a blade portion that is inserted transversely into the bone, e.g., into the trochanter above the fracture line in the femur, and a plate portion that may be positioned against and secured to the bone below the fracture line. The first bone fixation device is inserted into and mounted to the bone. The width of the blade portion of the first bone fixation device is preferably narrow (i.e., in the direction transverse to the longitudinal length of the blade portion) and is therefore able to rotate or otherwise be manipulated such that the plate portion of the first bone fixation device is positioned at a desired orientation along the bone (e.g., preferably it extends essentially parallel to the longitudinal axis of the bone). With the plate positioned at a desired orientation and fixed to the bone, e.g., by screws, the first bone fixation member may now be used as a guide to position the second bone fixation device. In a preferred embodiment, the width of the blade portion of the second bone fixation device is wider then that of the first blade portion and may accept a substantial amount of the loading that is applied to the bone fixation system in use.

An advantage of this system is that a blade portion that may be reoriented in the bone without having to increase or substantially increase the slot that is cut into the bone for the first blade portion is utilized. The plate of the first bone fixation device is utilized to orient the first blade portion. As the first plate portion is oriented along the exterior of the bone, the first blade portion may rotate in the bone. The first blade portion may then be used to orient the second bone fixation device). For example, the first blade portion may interact with the blade of the second bone fixation device so as to orient the second blade and, accordingly, to correctly align the second plate along the exterior of the bone.

According to such an aspect, a bone fixation system is provided that comprises a first fixation device. The first fixation device comprises a first longitudinally extending bone insertion blade having an orienting portion, and a first plate extending transversely from the first bone insertion blade and positionable along a surface of a bone. The bone fixation system further comprises a second fixation device. The second fixation device comprises a second longitudinally extending bone insertion blade orientatively interactive with the orienting portion, and a second plate extending transversely from the second bone insertion blade and positionable along the surface of the bone adjacent the first plate. When assembled, the second bone insertion blade has an orientation that is based on an orientation of the orienting portion.

The first bone insertion blade may be generally rounded in transverse section. The second bone insertion blade may be planar.

Each of the first bone insertion blade and the second bone insertion blade may have a transverse width, and the transverse width of the second bone insertion blade may be at least twice the transverse width of the first bone insertion blade.

The orienting portion may comprise a longitudinally extending groove. The groove may be C-shaped, and may have a longitudinally extending side opening having a height. The second bone insertion blade may comprise a tongue portion slidably insertable in the groove. The tongue portion may extend longitudinally along the second bone insertion blade. The tongue portion may have a thickness greater than the height of the longitudinally extending side opening. The tongue portion may be non-rotatably received in the groove to orient the second bone insertion blade with respect to the first bone insertion blade.

The first plate may comprise a first plate keyed surface, and the second plate may comprise a second plate keyed surface positionable in facing relation to and mateable with the first plate keyed surface.

The first plate and the second plate may be elongate in transverse section. The first plate and the second plate may each comprise a plurality of screw-holes extending therethrough.

The first bone insertion blade and the first plate may be integrally formed. The second bone insertion blade and the second plate may be integrally formed.

The bone fixation system may further comprise a slot formation guide removably mountable to the first fixation device. The slot formation guide may comprise a mounting portion and a template portion. The template portion may comprise a guide for a slot. The guide for the slot may have an orientation that is determined by the particular orientation of the first blade.

The template portion may comprise a plurality of linearly arranged apertures.

According to another aspect, the first bone fixation device may then be used to assist a doctor to cut a hole in the bone for the second blade portion such that the second plate portion is correctly oriented when the second bone fixation device is installed in and mounted to the bone. For example, a guide may be attached to the first bone fixation device, such as the first blade, and used as a template to cut a hole in the bone for the blade of the second bone fixation device.

In accordance with this aspect a bone fixation system is provided that comprises a first fixation device. The first fixation device comprises a first longitudinally extending bone insertion blade, and a first plate extending transversely from the first bone insertion blade and positionable along a surface of a bone. The bone fixation system further comprises a second fixation device. The second fixation device comprises a second longitudinally extending bone insertion blade interengageable with the first fixation device, and a second plate extending transversely from the second bone insertion blade and positionable along the surface of the bone. The bone fixation system further comprises a slot formation guide removably mountable to the first fixation device. The slot formation guide further comprises a template portion. The template portion has an orientation determined by an orientation of the first blade.

The first bone insertion blade may be generally rounded in transverse section. The second bone insertion blade may be planar.

Each of the first bone insertion blade and the second bone insertion blade may have a transverse width, and the transverse width of the second bone insertion blade may be at least twice the transverse width of the first bone insertion blade.

The second bone insertion blade may comprise a tongue portion slidably insertable in the first fixation device.

According to another aspect, a method of repairing a bone is provided. The method comprises (a) inserting a first blade of a first fixation device into a portion of the bone and positioning a first plate of the first fixation device along a surface of the bone, whereby the first blade is positioned in a particular orientation; and (b) inserting a second blade of a second fixation device into the portion of the bone adjacent the first blade at an orientation determined by the particular orientation of the first blade, and positioning a second plate of the second fixation device along the surface of the bone.

Step (b) may comprise interengaging the first and second blades. Step (b) may comprise interengaging the first and second blades while inserting the second blade into the bone.

The first blade may extend along a blade longitudinal axis, and step (a) may comprise: forming a first hole into the bone; inserting the first blade into the first hole; and, rotating the first fixation device about the longitudinal axis to align the first plate with the surface of the bone.

The method may further comprise securing the first fixation device to the bone.

Step (b) may comprise: forming a slot into the bone adjacent the first hole, wherein the slot has an orientation based on the particular orientation of the first blade; and, inserting the second blade into the slot.

The method may further comprise mounting a slot formation guide to the first fixation device and using the slot formation guide to form the slot in the bone. A mounting portion of the slot formation guide may be inserted into an orienting portion of the first fixation device, and the mounting portion of the slot formation guide may be removed from the orienting portion prior to inserting the second blade into the slot.

The method may further comprise positioning a second plate of the second fixation device along the surface of the bone adjacent the first plate and securing the second fixation device to the bone.

The bone may be the femur, and the portion of the bone may be the trochanter of the femur. The method may further comprise inserting the blades into the trochanter and positioning the plates along the femur.

DRAWINGS

Reference is made in the description below to the appended drawings, in which:

FIG. 8 is a perspective illustration showing a fifth step of the method of FIG. 4; and, FIG. 9 is a perspective illustration showing a sixth step of the method of FIG. 4.

DESCRIPTION OF VARIOUS EXAMPLES

Various apparatuses or methods will be described below to provide an example of each claimed invention. No example described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any claimed invention.

Figures 1A, 1B, 1C:
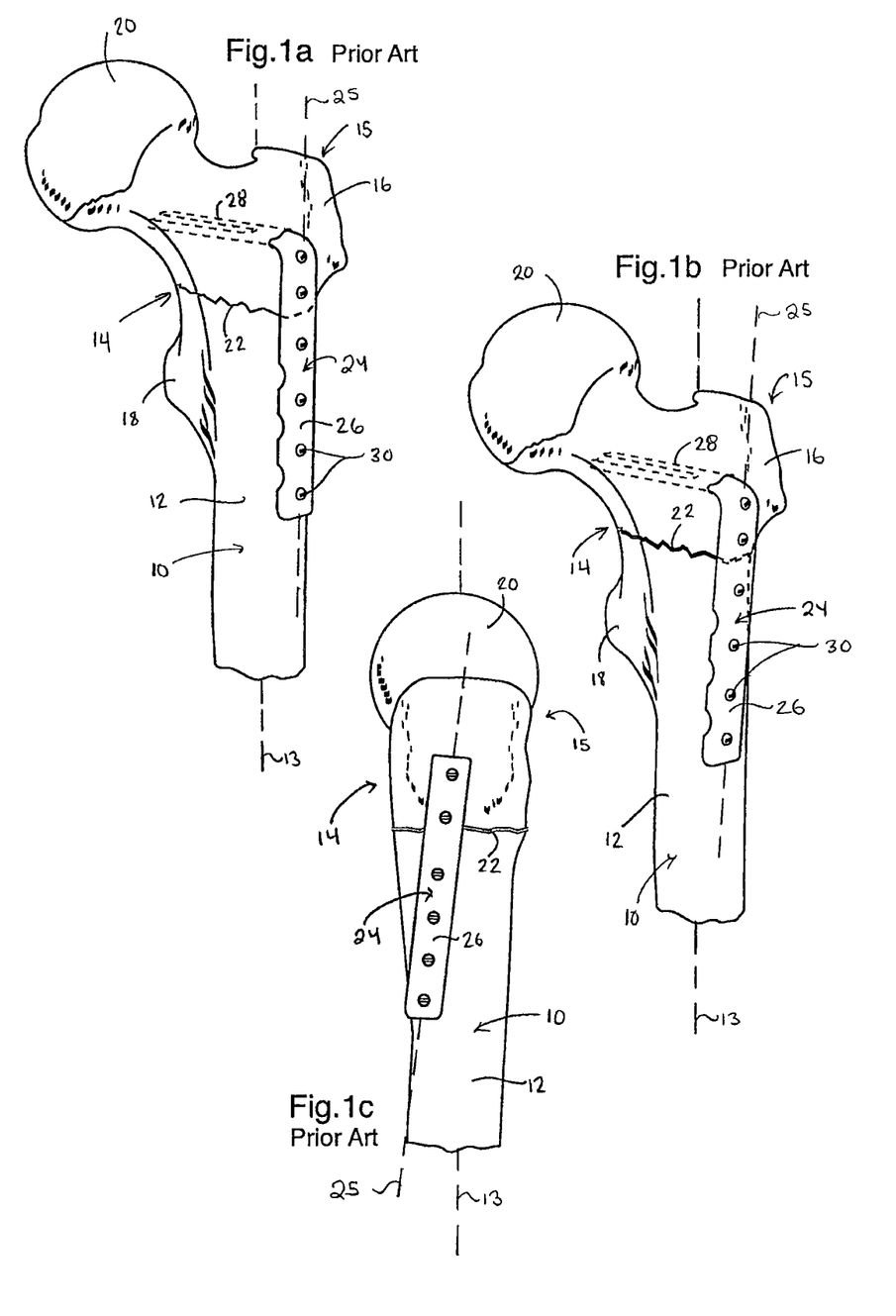
FIG. 1A is side perspective illustration of a prior art device that has been inserted into a femur.
FIG. 1B is side a perspective illustration of the prior art device of FIG. 1A, inserted into a femur and misaligned with the femur.
FIG. 1C is a front plan view of the prior art device of FIG. 1A, inserted into a femur and misaligned with the femur.

Referring to FIG. 1A, a human femur 10 is shown. A human femur 10 generally comprises a body 12, which extends along an axis 13 between a proximal femur 15 and a distal femur (not shown). The proximal femur 15 comprises a trochanter region 14, which comprises a greater trochanter 16, and a lesser trochanter 18, and a head 20. Breaks, such as break 22, can occur in the proximal femur 15 near the trochanter region 14. A prior art device 24 usable in the repair of such breaks is shown in FIG. 1A. Such a device is described in U.S. Pat. No. 7,316,687 (Aikins et al.), mentioned hereinabove. The device 24 comprises a plate portion 26, and a blade portion 28 extending transversely to the plate portion 26. In use, a slot is drilled into the trochanter region 14 of the bone. In an ideal procedure, the slot is drilled at a 90° angle to the axis 13 of the bone. A drill guide (not shown) may be used in order to achieve this angle. The blade portion 28 is inserted into the slot, until the plate portion 26 abuts the body 12 of the bone. The plate portion 26 is then secured to the bone, for example using one or more screws 30. In an ideal procedure, after the blade 28 is inserted into the bone, the longitudinal axis 25 of the plate 26 is parallel to the axis 13 of the bone, and is aligned along the exterior of the body 12 of the bone, as shown in FIG. 1A.

However, referring to FIGS. 1B and 1C, a common occurrence is that after the slot is drilled and the blade portion 28 is inserted into the slot, the longitudinal axis of the plate portion 26 does not align with the axis 13 of the bone. This can be due to the variation in the anatomy of the patient, or to the slot not being cut at the required angle. For example, even if the slot is drilled at a 90° angle to the axis 13, due to the anatomy of the patient, the plate portion 26 may not align with the bone. Alternately, the slot may not have been drilled at a perfect 90° angle. This can readily occur even with the use of a drill guide. When the plate portion 26 fails to align with the axis 13 of the bone and the plate is not aligned along the body 12 of the bone 10, as exemplified in FIG. 1C, the device 24 must be removed from the bone, and the procedure must be restarted by drilling a second slot in the trochanter region 14. Drilling the second slot introduces further injury to the bone. In addition, on the second attempt, the plate portion 26 may still not align with the axis 13 of the bone.

The device 24 may additionally be used to repair alternate problems in bones, such as congenital defects. Further, the device 24 may be used in alternate bones, such as in the proximal humerus, or the distal tibia, for example. The problem of misalignment with the body of the bone commonly occurs in these situations as well.

Figure 2:
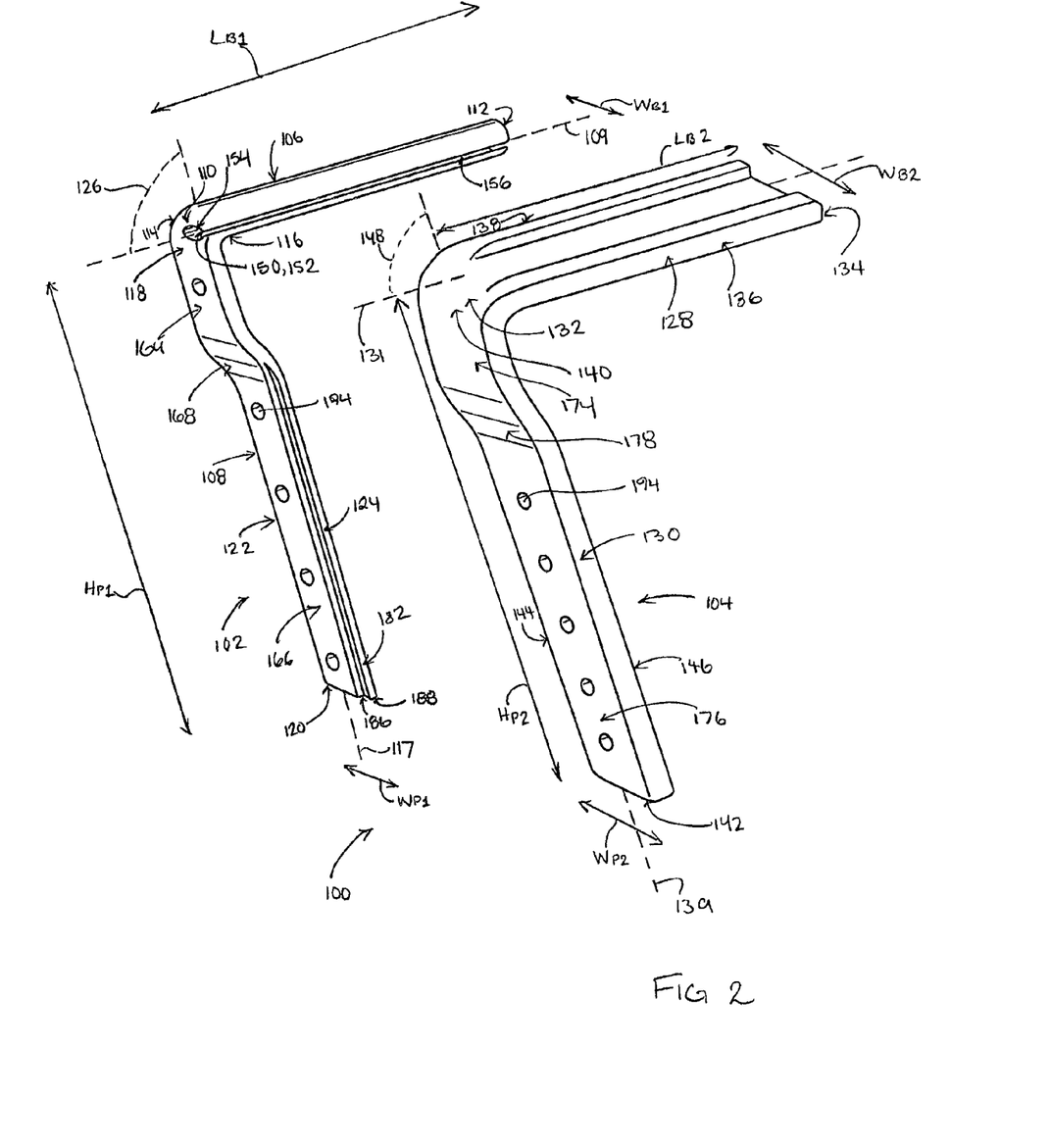
FIG. 2 is an exploded perspective right-side view of an example of a bone fixation system of the present disclosure.

Referring now to FIG. 2, an example of a bone fixation system 100 of the present application is shown. The exemplified bone fixation system 100 is configured for use in repair of a proximal femur 15, and a specific example of the use of the system 100 in a proximal femur 15 will be described. However, it will be appreciated that the system 100 may be used in other bones, such as the distal femur, proximal humerus, or the distal tibia, for example. The system 100 may also be used in ankle fusion. As will be described hereinbelow, the bone fixation system 100 of the present application may reduce, minimize, or prevent the occurrence of misalignment with the bone.

Referring still to FIG. 2, the bone fixation system 100 comprises a first fixation device 102, and a second fixation device 104. The first fixation device 102 may also be referred to herein as a reduction plate 102, and the second fixation device 104 may also be referred to herein as a fixed angle plate 104. As exemplified, the first fixation device 102 and second fixation device 104 are separately formed. As will be described in further detail hereinbelow, the first fixation device 102 is configured such that the orientation thereof is adjustable when the first fixation device 102 is inserted into the bone. The second fixation device 104 is preferably interengageable with and assemblable to the first fixation device 102, whereby the orientation of the second fixation device 104 is determined by the orientation of the first fixation device 102. Accordingly, the first fixation device 102 generally serves as an orienting guide for the bone fixation system 100, to prevent or reduce the occurrence of misalignment with the bone.

Referring still to FIG. 2, the first fixation device 102 comprises a first bone insertion blade 106 (also referred to herein as a first blade 106), and a first plate 108 extending transversely from the first blade 106. The first blade 106 is insertable into a bone, such as a proximal femur, and the first plate 108 is positionable along the surface of the bone, as will be described in further detail hereinbelow. The first bone insertion blade 106 extends longitudinally along a longitudinal axis 109 between a front end 110, and a rear end 112, and laterally between an outer side 114 and an inner side 116. A length $L_{B1}$ of the first bone insertion blade 106 is defined between the front end 110 and the rear end 112, and a width $W_{B1}$ is defined between the outer side 114 and the inner side 116. The first plate 108 extends longitudinally along an axis 117 between a top end 118, and a bottom end 120, and laterally between an outer side 122 and an inner side 124. Although the first plate 108 may not extend linearly (e.g., it may have a bend portion 168 as will be described further hereinbelow), the longitudinal axis 117 is defined as the axis along which the linear lower portion 166 of the first plate 108 extends. A height $H_{P1}$ of the first plate 108 is defined between the top end 118 and the bottom end 120, and a transverse width $W_{P1}$ of the first plate 108 is defined between the outer side 122 and the inner side 124. The top end 118 of the first plate 108 is joined to the front end 110 of the first blade 106, and the first plate 108 extends transversely and downwardly from the first bone insertion blade 106. Preferably, the longitudinal axis 117 is at an angle 126 of between about 90 and 140 degrees with respect to the first blade 106. As shown, the longitudinal axis 117 is at an angle of 90 to 110 degrees with respect to the first blade 106.

Similarly, referring still to FIG. 2, the second fixation device 104 comprises a second bone insertion blade 128 (also referred to herein as a second blade 128), and a second plate 130 extending transversely from the second blade 128. The second blade 128 is insertable into the bone adjacent the first blade 106 and is preferably interengageable with the first blade 106, and the second plate 130 is positionable along the surface of the bone, adjacent the first plate 108, as will be described in further detail hereinbelow. The second blade 128 extends longitudinally along a longitudinal axis 131 between a front end 132, and a rear end 134, and laterally between an outer side 136 and an inner side 138. A length $L_{B2}$ of the second bone insertion blade 128 is defined between the front end 132 and the rear end 134, and a width $W_{B2}$ is defined between the outer side 136 and the inner side 138. The second plate 130 extends longitudinally along an axis 139 between a top end 140, and a bottom end 142, and laterally between an outer side 144 and an inner side 146. Although the second plate 130 may not extend linearly (e.g., it may have a bend portion 178 as will be described further hereinbelow), the longitudinal axis 139 is defined as the axis along which the linear lower portion 176 of the second plate 130 extends. A height $H_{P2}$ of the second plate 130 is defined between the top end 140 and the bottom end 142, and a transverse width $W_{P2}$ of the second plate 130 is defined between the outer side 144 and the inner side 146. The top end 140 of the second plate 130 is joined to the front end 132 of the second blade 128, and the second plate 130 extends transversely and downwardly from second blade 128. The longitudinal axis 139 of the second plate 130 is preferably at an angle 148 with respect to the first blade 128 that is the same as angle 126. For example, the angle may be between about 90 and 140 degrees. As shown, the longitudinal axis 139 of the second plate 130 is at an angle of 90 to 110 degrees with respect to the second blade 128.

It will be appreciated that in alternate examples, wherein the bone fixation system 100 is configured for use in another bone, the first 102 and second 104 fixation devices may be configured in another manner, preferably to match the contour of the exterior surface of the bone that is to be repaired. For example, if the bone fixation system 100 is configured for use in the distal tibia, the first plate 108 may extend upwardly from the first blade 106 (i.e. the device may be rotated 180°), and the second plate 130 may extend upwardly from the first blade 128.

As exemplified, the first blade 106 and the first plate 108 are preferably integrally formed. Further, the second blade 128 and second plate 130 are preferably integrally formed. In alternate examples, the first blade 106 and first plate 108 may be separately formed, and may be securable together. Similarly, the second blade 128 and second plate 130 may be separately formed, and may be securable together. It will be appreciated that the first 102 and second 104 fixation devices maybe manufactured in any manner known in the art and may be made of any materials known in the art. Preferably, they are made from stainless steel, however other materials may also be used.

Figures 3, 3A:
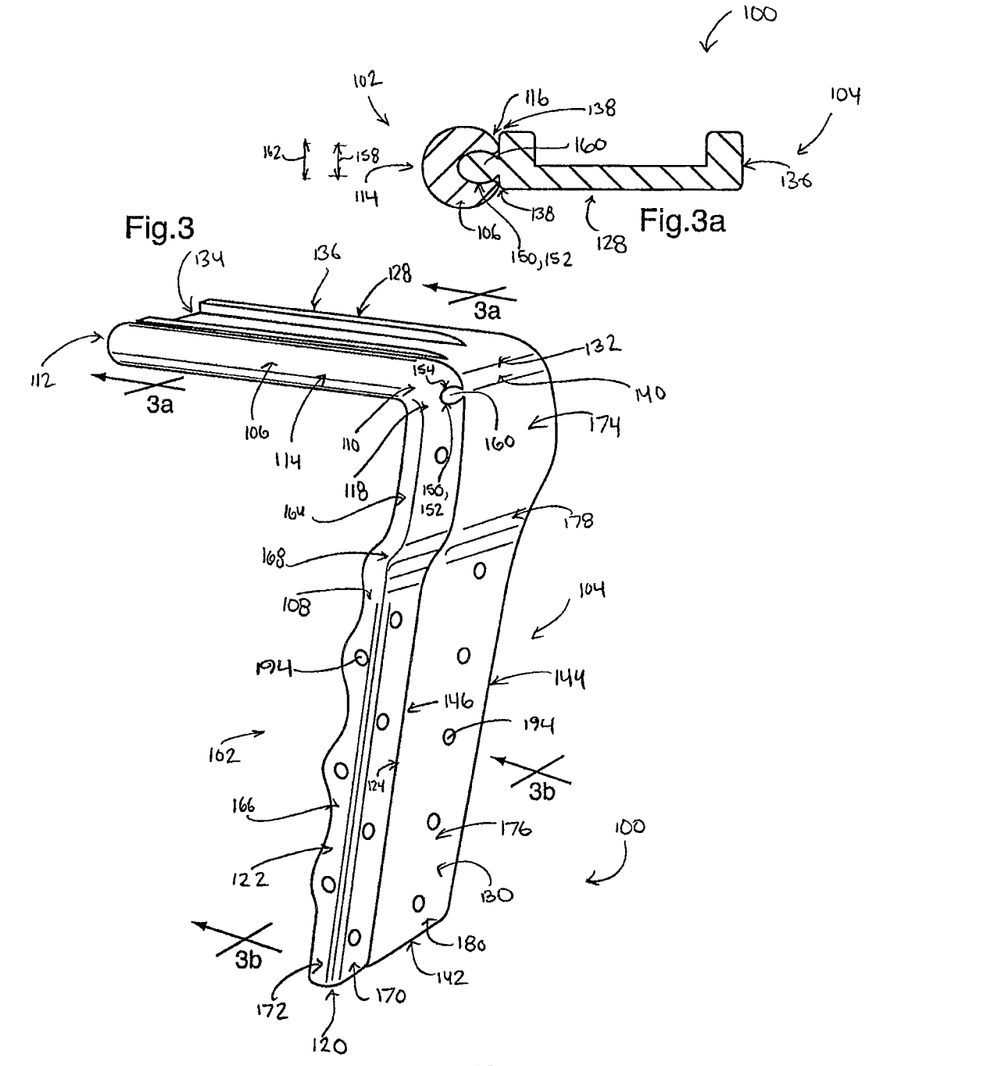
FIG. 3 is an assembled perspective left-side view of the bone fixation system of FIG. 2.
FIG. 3a is a cross section taken along line 3a-3a in FIG. 3.

As exemplified in FIGS. 3, and 3a, the first blade 106 is generally rounded in transverse section. As will be described in more detail hereinbelow, this allows the orientation of the first fixation device 102 to be adjusted when it is positioned in a bone. As exemplified, the first blade 106 is generally circular in cross section. In alternate examples, the first blade 106 may be slightly ovoid. In further alternate examples, the first blade 106 may be any suitable shape that allows for the orientation of the first fixation device 102 to be adjusted when it is inserted into a bone. It will be appreciated that if the slot into which the first blade is inserted in slightly oversized, then the first fixation device 102 may be rotated about blade 106 even if the first blade 106 is not rounded in transverse section. Provided $W_{B1}$ is relatively short, e.g., from 2 to 14 mm, preferably from 4 to 8 mm. The orientation of first fixation device 102 may be adjusted when the first blade 106 is positioned in the bone without damaging the structural integrity of the bone.

In contrast, referring still to FIGS. 3 and 3a, the second blade 128 is preferably generally planar or flat in transverse section. Accordingly, when the second blade 128 is inserted into the bone, the orientation of the second fixation device 104 is preferably not adjustable. Preferably, as shown, the width $W_{B2}$ (shown in FIG. 2) of the second blade 128 is at least twice, and in some embodiments even more than twice the width $W_{B1}$ (shown in FIG. 2) of the first blade 106. Width $W_{B2}$ may be from 5 to 40 mm, preferably from 10 to 30 mm.

As mentioned hereinabove, the first fixation device 102 serves as an orienting guide for the second fixation device 104. This may be achieved by the first fixation device 102 being interengageable with the second fixation device 104. Referring still to FIGS. 3, and 3a, the first blade 106 comprises an orienting portion 150, and the second blade 128 is orientatively interactive with the orienting portion 150, so that when the first fixation device 102 and second fixation device 104 are assembled, the second blade 128 has an orientation that is based on an orientation of the orienting portion 150.

Figure 3B:
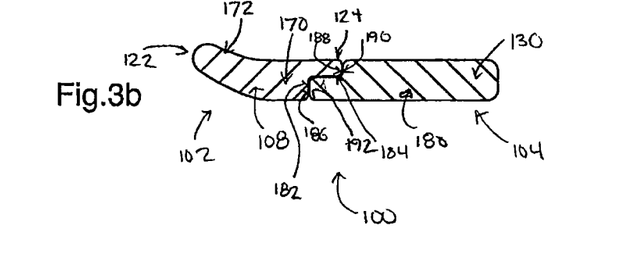
FIG. 3b is a cross section taken along line 3b-3b in FIG. 3.

As exemplified, the orienting portion 150 is a longitudinally extending groove 152. The groove 152 extends along the length $L_{B1}$ (shown in FIG. 2) of the first blade 108, to an opening 154 at the front end 110 of the first insertion blade 108. The groove 152 may optionally extend to another opening (not shown) at the rear end 112 of the first insertion blade 106. The groove 152 is adjacent the inner side 116 of the first insertion blade 106, and comprises a longitudinally extending side opening 156 (shown in FIG. 2), which has a height 158, and which extends along the length $L_{B1}$ of the first insertion blade 108. As can be seen in FIG. 3b, the groove 130 is preferably generally C-shaped.

Referring still to FIGS. 3 and 3a, the second blade 128 comprises a tongue portion 160, which is slidably insertable into the groove 152. The tongue portion 160 is generally longitudinally extending, and extends along the inner side 138 of the second blade 128, from the front end 132 of the second blade 128 to the rear end 134 of the second blade. The tongue portion 160 has a height 162, which is greater than the height 158 of the groove 152. Accordingly, the tongue portion 160 may only be inserted into the groove 152 by inserting the tongue portion 160 into the opening 154, and sliding the tongue portion 160 longitudinally into the groove 152.

Referring to FIG. 3a, the tongue portion 160 and the groove 152 are configured such that when the tongue portion 160 is received in the groove 152, the second blade 128 is at a particular orientation with respect to the first blade 106. Preferably, as shown, the tongue portion 160 and groove are dimensioned such that the tongue portion 160 is non-rotatably receivable in the groove 152. For example, as exemplified, both the tongue portion 160 and the groove 152 may be generally ovoid, so that the tongue portion 160 may not rotate within the groove 152. Accordingly, when the tongue portion 160 is received in the groove 152, the second blade 128 is non-rotatable with respect to the first blade, and is oriented at a particular orientation with respect to the first blade 106. That is, the orientation of the second blade 128 is based on the orientation of the orienting portion 150. For example, as shown in FIG. 3a, the orienting portion is oriented such that the side opening 156 is open towards the right hand side of the figure; accordingly, the second blade 128 is generally horizontal. However, if the first blade were rotated about axis 109 (shown in FIG. 2), the orienting portion 150 would be oriented such that the side opening 156 is open to the top of the figure, and the second blade 128 would be generally vertical.

In alternate examples the orienting portion 150 may comprise a notch, a slot, an abutment surface, or any other structure, which interacts with the second fixation device 104 so that the second blade 128 has an orientation that is based on the orientation of the orienting portion 150. For example, the orienting portion 150 may comprise a generally planar abutment surface at the inner side 116 of the first blade 106, and the second blade 128 may comprise a generally planar mating abutment surface at the inner side 138 thereof. When the abutment surface and the mating abutment surface are in an abutted configuration, the second blade 128 is at a particular orientation with respect to the first blade 106.

Further, in the example shown, the interengagement of the tongue portion 160 and the groove 152 serves to generally lock the first fixation device 102 to the second fixation device 104. In alternate examples, when the bone fixation system 100 is assembled, the first fixation device 102 may not be locked to the second fixation device. For example, if the orienting portion 150 comprises a generally planar abutment surface at the inner side 116 of the first blade 106, and the second blade 128 comprises a generally planar mating abutment surface at the inner side 138 thereof, the abutment of the abutment surface and the mating abutment surface will not serve to lock the first fixation device 102 and the second fixation device 104 together.

It will be appreciated that when the second bone fixation device 104 is assembled to the first bone fixation device 102 or the blade 128 is positioned in the bone after having been oriented using the first bone fixation device 102, the orientation of the second blade 128 may be somewhat modifiable with respect to the orientation of the first blade 106. This may be due, for example, to tolerances required in manufacturing the first 102 and second 104 bone fixation devices and/or the size of the slot provided in the bone for blade 128. For example, the orientation of the second blade 128 may be modifiable by up to about 10° with respect to the first blade 106. Preferably, the orientation of the second blade 128 is modifiable by no more than about 5° with respect to the first blade 106.

Referring still to FIGS. 3, 3a, and 3b, each of the first plate 108 and the second plate 130 are preferably configured for lying along the surface of a bone. As exemplified, the first plate 108 is generally flattened and is elongate in transverse section. As shown, the first plate 108 is contoured from the top end 118 to the bottom end 120. Specifically, as mentioned hereinabove, the first plate 108 comprises an upper portion 164, and a lower portion 166. As can be seen in FIG. 3, the lower portion 166 is offset inwardly (i.e. in a direction towards the rear end 112 of the first insertion blade 106) with respect to the upper portion 164, and a bend portion 168 is provided between the upper portion 164 and the lower portion 166. This allows the upper portion 164 to lie along the trochanter region 114 of the bone, while the lower portion lies along the body 12 of the bone.

Referring still FIGS. 3 and 3b, the lower portion 166 of the first plate 108 may comprise a generally straight portion 170 adjacent the inner side 124, and a curved portion 172 adjacent the outer side 122. That is, the lower portion 166 of the first plate 106 is non-linear between the inner side 124 and the outer side 122. The curved portion 172 is configured to generally match the shape of the femur, so that in use, the lower portion 166 lies generally flush against the femur.

Similarly, the second plate 130 is generally flattened, for lying along the surface of the bone, and is generally elongate in transverse section. The second plate 130 is contoured from the top end 140 to the bottom end 142, and the contour matches the contour of the first plate 108. Specifically, as mentioned hereinabove, the second plate 130 comprises an upper portion 174, and a lower portion 176. As can be seen in FIG. 3, the lower portion 176 is offset inwardly (i.e. in a direction towards the rear end 134 of the second insertion blade 128) with respect to the upper portion 174, and a bend portion 178 is provided between the upper portion 174 and the lower portion 176. This allows the upper portion 174 to lie along the trochanter region of the bone, while the lower portion 176 lies along the body 12 of the bone.

Referring still FIGS. 3 and 3b, the lower portion 176 of the second plate 130 comprises only a generally straight portion 180, extending between the inner side 146 and the outer side 144.

In alternate examples, wherein the bone fixation system 100 is configured for use with other bones, the first plate 108 and second plate 130 may have another shape. For example, the first plate 108 and/or the second plate 130 may be generally straight between their top ends 118, 140, respectively, and their bottom ends 120, 142, respectively. Alternately, the first plate 108 and/or the second plate 130 may comprise a bend portion of another shape. Further, the lower portion 166 of the first plate 108 may comprise only a straight portion 170, or may comprise only a curved portion 172, or may comprise a curved portion 172 of another shape. Further, the lower portion 176 of the second plate 130 may comprise a curved portion. It will also be appreciated that the configuration of the lower portions 170, 176, inner sides 124, 146 and the outer sides 122, 144 may be of any desired configuration.

Preferably, as exemplified in FIGS. 2 and 3b, the first plate 108 and the second plate 130 are preferably mateable. Accordingly, the first plate 108 may further comprise a first plate keyed surface 182, and the second plate comprises a second plate keyed surface 184, which is positioned in facing relation to and is mateable with the first plate keyed surface 182. The keyed surfaces 182, 184 interengage and mate when the first bone fixation device 102 and second bone fixation device 104 are assembled together. The first plate keyed surface 182 may be provided at the inner side 124 of the first plate 108, and on the lower portion 166 of the first plate 108. The second plate keyed surface 184 may be provided at the inner side 146 of the second plate 130, and on the lower portion 176 of the second plate 130. The keyed surfaces 182, 184 may be of any shape, which allows them to interengage and mate. Preferably, as shown, the keyed surfaces 182, 184 are of a shape that allows them to interact and mate when the tongue 160 is slid into the groove 152 in a direction parallel to the axes 109 and 131. As shown, the first plate keyed surface 182 may be stepped, including a first recess 186 and a first protrusion 188, and the second plate keyed surface may also be stepped, including a second recess 190 and a second protrusion 192. When the first bone fixation device 102 and second bone fixation device 104 are assembled together, as shown in FIG. 3b, the first protrusion 188 is received in the second recess 190, and the second protrusion 192 is received in the first recess 186.

In alternate examples, the keyed surfaces 182, 194 may be of any another suitable shape. In further alternate examples, keyed surfaces may not be provided. For example, the inner sides 124, 138 of the first 108 and second 130 plates may each comprise a single planar surface, and the single planar surfaces may be in facing relation to each other when the first fixation device is assembled to the second fixation device.

The first plate 108 and the second plate 130 may be secured to a bone by any means known in the art. As exemplified in FIG. 3, the first plate 108 and the second plate 130 each comprise a plurality of screw-holes 194 extending therethrough. The screw holes 194 may be provided on the upper portions 164, 174 of the plates 128, 130, or the lower portions 166, 176 of the plates 128, 130, or both. Preferably, at least some of the screw holes 194 are provided on the curved portion 172 of the first plate 108.

Referring now to FIGS. 4 to 9, a method of repairing a bone using the bone fixation system 100 will be described. The method will be described with relation to repairing a broken femur, such as the broken femur 10 shown in FIG. 1. However, as noted hereinabove, the method may be used in other bones, and to repair conditions other than breaks. As will be described in further detail, the method generally comprises (a) inserting the first blade 106 of the first fixation device 102 into a portion of the bone and positioning the first plate 108 of the first fixation device 102 along the surface of the bone; and (b) inserting a second blade 128 of a second fixation device 104 into the portion of the bone adjacent the first blade 106 and positioning a second plate 130 of the second fixation device 104 along the surface of the bone. The first blade 106 is positioned in the bone at a particular orientation, and the second blade 128 is positioned at an orientation that is determined by the particular orientation of the first blade 128.

Figures 4, 5:
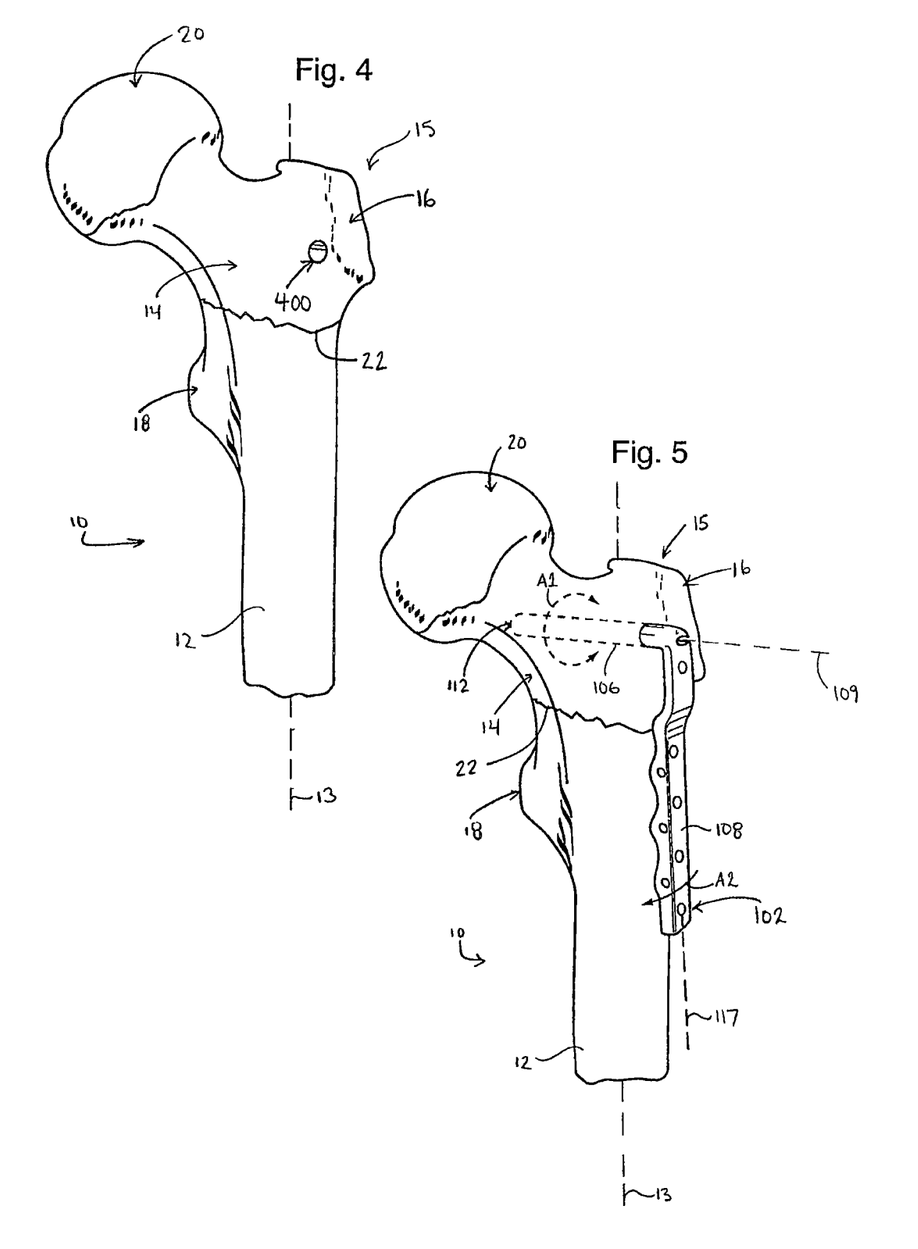
FIG. 4 is a perspective illustration showing a first step of an example of a method for repairing a bone according to the present disclosure.
FIG. 5 is a perspective illustration showing a second step of the method of FIG. 4.

Referring to FIG. 4, as a first step, a first hole 400 may be formed into a portion of the femur, such as the trochanter region 14, as shown. The first hole 400 may be formed by drilling, optionally using a guidewire and a cannulated drill, as is known in the art. As shown, the first hole 400 is rounded, and is preferably circular. However, first the hole 400 may alternately be ovoid, or another suitable shape suitable for receiving first blade 106 and enabling first blade 106 to be rotatable therein. The first hole 400 may have a depth and circumference selected based on the size of the bone.

Referring to FIG. 5, as a second step, the first blade 106 may be inserted into the first hole 400. The first blade 106 may be inserted until the rear end 112 of the first blade 106 contacts the end of the first hole 400, and the first plate 108 contacts the surface of the femur 10. The orientation of the first fixation device 102 may then be adjusted. As the first blade 106 is preferably rounded in transverse section, the first blade 106 may be rotatable within the hole 400. Accordingly, the first fixation device 102 may be rotated about the longitudinal axis 109, in a direction indicated by arrows A1 and A2, to align the axis 117 of the first plate 108 with the axis 113 of the bone 10, so that the first plate 108 is aligned along the femur 10. It will be appreciated that if slot 400 is sufficiently large other motions other that rotation, e.g., translation, may be used.

Prior to or subsequent to inserting the first blade 106 into the femur 10 and adjusting the angle of the first fixation device 102, the break 22 in the bone may be provisionally reduced, optionally using K-wires as is known in the art, and the reduction may be checked under fluoroscopy. Alternately, the reduction may be done after insertion the first blade 106 into the femur 10, but before adjusting the orientation of the first fixation device 102.

Figures 6, 7:
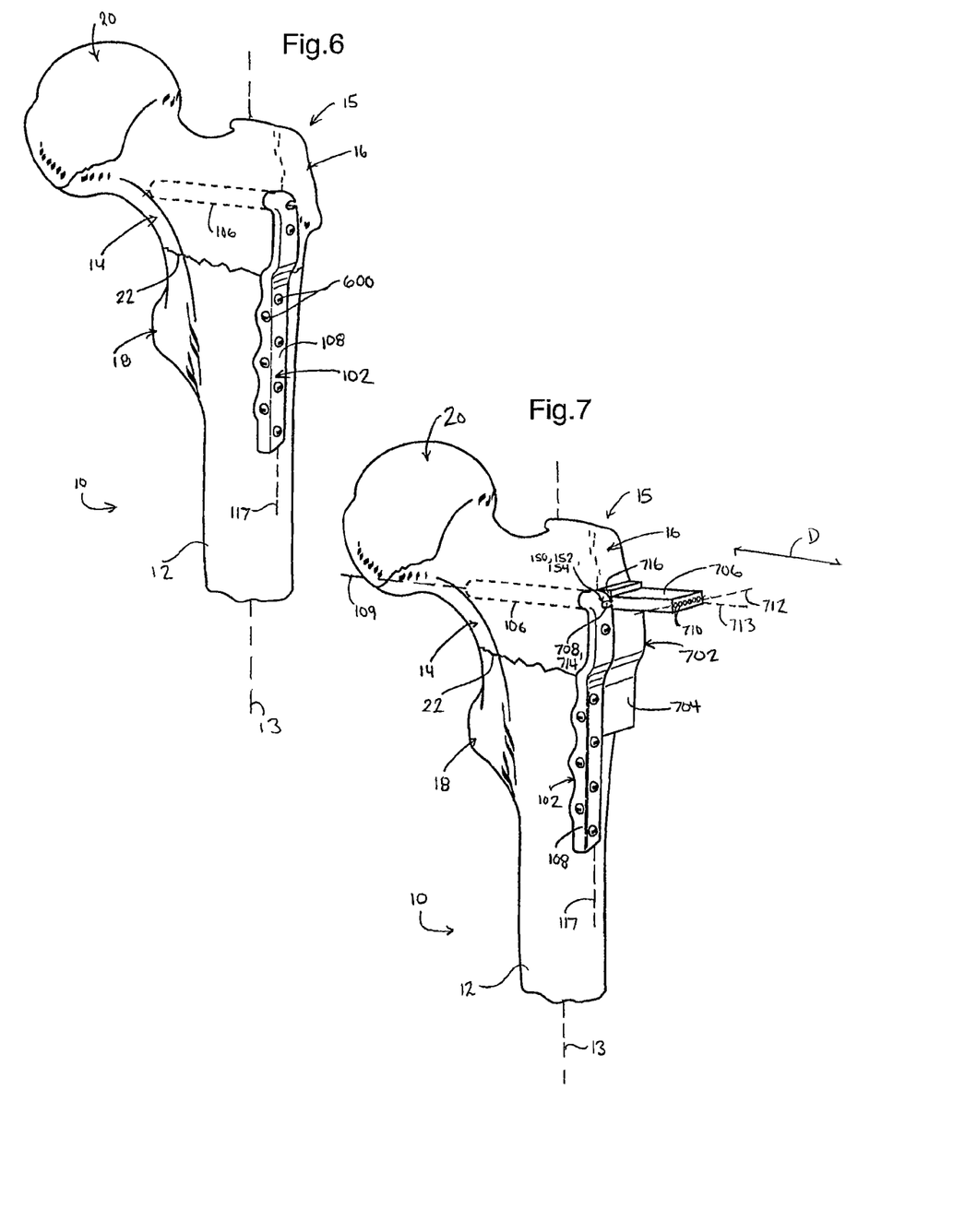
FIG. 6 is a perspective illustration showing a third step of the method of FIG. 4.
FIG. 7 is a perspective illustration showing a fourth step of the method of FIG. 4.

Referring to FIG. 6, the first fixation device 102 may then be secured to the bone. For example, a plurality of additional holes may be formed in the bone, aligned with the screw holes 194 of the first plate 108. Screws 600 may then be screwed through the screw holes 194, and into the bone.

Figures 8, 9:
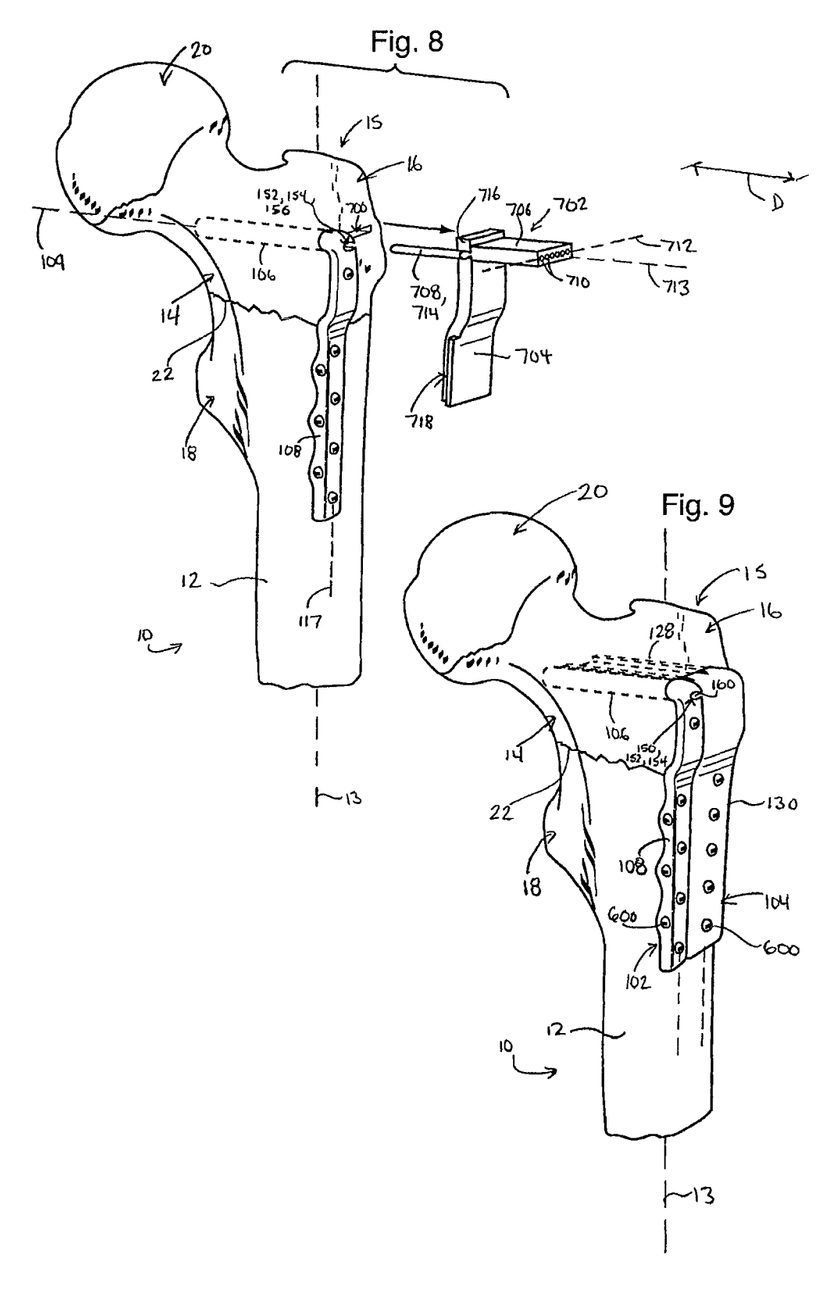

Referring to FIGS. 7 and 8, a slot 700 (shown in FIG. 8) may then be formed in the bone 10 adjacent the first hole 400, and generally parallel to the first blade 106. Optionally, a slot formation guide 702 may be used to form the slot in the bone. Slot formation guide 702 may interact with first fixation device 102, and preferably with first blade 106. Accordingly, the first fixation device 102 may be utilized to orient the opening for the second fixation device 104, and thereby orient second fixation device 108. In such a case, second fixation device 108 need not interact with first fixation device 102 when blade 106 is inserted into the bone.

As exemplified, the slot formation guide 702 may generally comprise a body portion 704, a template portion 706, and a mounting portion 708. The body portion 704 is preferably shaped similarly to the second plate 130. The template portion 706 extends from the body portion 704, and may comprise one or more openings through which a drill bit may be passed, to drill one or more holes in the bone. As shown, the template portion 706 comprises a plurality of circular holes 710, which are linearly arranged along a lateral axis 712, and which have a depth D extending along a longitudinal axis 713. It will be appreciated that template portion 706 may alternately comprise a single opening that may be used as a guide to cut a hole for the second blade. Template portion 706 is preferably sized such that once used to cut a hole or a series of holes that are then joined together, the second blade may be received in the bone and, preferably the second blade is received in the bone at a fixed or generally fixed orientation. It will be appreciated that since the first fixation device is correctly oriented, the guide may be engageable with the first fixation device to ensure that the opening in the bone for the second blade is oriented such that, when the second blade is inserted into the bone, the second plate is correctly aligned along the bone. In such a case, the second fixation device 104 may be correctly aligned when the second blade is inserted and therefore the second blade need not interact with the first blade. However, it is preferred that the first and second fixation devices 102, 104 interengage as this may increase the permitted structural loading of the fixation system.

As exemplified, the mounting portion 708 is preferably configured to removably mount the slot formation guide 702 to the first fixation device 102, such that the template portion 706 is at an orientation determined by the orientation by the first blade 106. Preferably, the mounting portion 708 is configured to mount the slot formation guide 702 to the first fixation device 102 such that the lateral axis 712 is perpendicular to both the longitudinal axis 109 of the first blade 108, and the longitudinal axis 117 of the first plate 108, and such that the longitudinal axis 713 is parallel to the longitudinal axis 109.

Preferably the mounting portion 708 interacts with the first blade 106 and may interengage using the same means as the second blade. As exemplified, the mounting portion 708 may comprise a key 714, which is provided on a sidewall 716 of the body portion 704, and which extends perpendicular to the lateral axis 712. The key 714 is insertable into the groove 152, via the opening 154. Alternately, or in addition, the sidewall 716 of the body portion 704 may comprise a third keyed surface 718 (shown in FIG. 8). The third keyed surface 718 is preferably essentially identical in profile to the second plate keyed surface 184, and is configured to mate and interengage with the first plate keyed surface 184. Accordingly, the slot formation guide 702 may be mounted to the first fixation device 102 such that the key 714 is received in the groove 152, and such that the third keyed surface 718 is interengaged with the first plate keyed surface 182, as shown in FIG. 7. When the slot formation guide 702 is in this position, the lateral axis 712 may extend perpendicular to both the longitudinal axis 109 of the first blade 108, and the longitudinal axis 117 of the first plate 108. Further, the longitudinal axis 713 may extend parallel to the axis 109. The slot formation guide 702 may then be used to form the slot 700 in the bone, e.g., by passing a drill bit through each of the holes 710, to drill a line of holes (not shown) in the bone. Referring to FIG. 8, the slot formation guide 702 may then be removed from the first fixation device 102, and the holes in the bone may then be connected, for example, by using a chisel (not shown), to form the slot 700. The resulting slot 700 will extend parallel to the longitudinal axis 109 of the first blade 106.

Referring now to FIG. 9, the second blade 128 may then be inserted into the slot 700. Preferably, the second blade 128 may be inserted into the slot 700 while interengaging the first 106 and second 128 blades. Specifically, the tongue 160 may be inserted into the groove 150 through the opening 154, while the second blade 128 is inserted into the slot. The second blade 128 may be inserted until the second plate 130 contacts the surface of the bone 10 and is positioned along the surface of the bone 10 adjacent the first plate 108, and the second keyed surface 184 interengages with the first keyed surface 182.

Referring still to FIG. 9, the second fixation device 104 may then be secured to the bone 10. For example, a plurality of additional holes may be formed in the bone, aligned with the screw holes 194 of the second plate 130. Screws 600 may then be screwed through the screw holes 94, and into the bone. It will be appreciated that second fixation device may be secured to the bone by any means known in the art.

Accordingly, as shown in FIG. 9, the first 102 and second 104 bone fixation devices are positioned adjacent each other and are secured to the bone. Further, the longitudinal axes 117, 119 of the first 108 and second 130 plates are generally parallel with the axis 13 of the bone 12, and the first 108 and second 130 plates are aligned along the body 12 of the bone 10.

It will be appreciated that the slot formation guide 702 may be considered a part of the bone fixation system 100. For example, the first fixation device 102, second fixation device 704, and slot formation guide 702 may be sold together as a kit.

The invention claimed is:

1. A bone fixation system comprising:
   (a) a first fixation device comprising:
      (i) a first longitudinally extending bone insertion blade having an orienting portion, the first bone insertion blade insertable into a bone; and
      (ii) a first plate extending transversely from the first bone insertion blade and positionable along a surface of the bone when the first bone insertion blade is inserted into the bone, the first plate having
         a first plate first end located at the first bone insertion blade,
         a spaced apart first plate second end located distal to the first plate first end,
         a first plate bone-facing surface extending between the first plate first end and the first plate second end,
         a first plate outer surface extending between the first plate first end and the first plate second end and facing away from the bone, and
         a first plate side wall extending between the first plate bone-facing surface and the first plate outer surface; and
   (b) a second fixation device comprising:
      (i) a second longitudinally extending bone insertion blade insertable into the bone and orientatively interactive with the orienting portion, and
      (ii) a second plate extending transversely from the second bone insertion blade and positionable along the surface of the bone adjacent the first plate when the second longitudinally extending bone insertion blade is inserted into the bone, the second plate having
         a second plate first end located at the second bone insertion blade,
         a spaced apart second plate second end located distal to the second plate first end,
         a second plate bone-facing surface extending between the second plate first end and the second plate second end,
         a second plate outer surface extending between the second plate first end and the second plate second end and facing away from the bone facing surface, and
         a second plate side wall extending between the second plate bone-facing surface and the second plate outer surface;
   wherein, when assembled, the second bone insertion blade has an orientation that is based on an orientation of the orienting portion, and the first plate side wall and the second plate side wall are positioned side-by-side in facing relation to each other.

2. The bone fixation system of claim 1, wherein the first bone insertion blade is rounded in transverse section.

3. The bone fixation system of claim 2, wherein each of the first bone insertion blade and the second bone insertion blade has a transverse width and the transverse width of the second bone insertion blade is at least twice the transverse width of the first bone insertion blade.

4. The bone fixation system of claim 3, wherein the second bone insertion blade is planar.

5. The bone fixation system of claim 1, wherein the orienting portion comprises a longitudinally extending groove.

6. The bone fixation system of claim 5, wherein the second bone insertion blade comprises a tongue portion slidably insertable in the groove.

7. The bone fixation system of claim 6, wherein the tongue portion extends longitudinally along the second bone insertion blade.

8. The bone fixation system of claim 7, wherein the tongue is non-rotatably received in the groove to orient the second bone insertion blade with respect to the first bone insertion blade.

9. The bone fixation system of claim 5, wherein the groove is C-shaped.

10. The bone fixation system of claim 7, wherein the groove has a longitudinally extending side opening having a height and the tongue has a thickness greater than the height.

11. The bone fixation system of claim 1, wherein the first plate side wall comprises a first plate keyed surface and the second plate side wall comprises a second plate keyed surface positionable in facing relation to and mateable with the first plate keyed surface.

12. The bone fixation system of claim 1, wherein the first plate and the second plate are elongate in transverse section.

13. The bone fixation system of claim 1, wherein the first plate and the second plate each comprise a plurality of screwholes extending therethrough.

14. The bone fixation system of claim 1, wherein the first bone insertion blade and the first plate are integrally formed.

15. The bone fixation system of claim 14, wherein the second bone insertion blade and the second plate are integrally formed.

16. The bone fixation system of claim 1, further comprising a slot formation guide removably mountable to the first fixation device, the slot formation guide comprising a mounting portion and a template portion, wherein the template portion comprises a guide for a slot, the guide for the slot having an orientation that is determined by the orientation of the orienting portion.

17. The bone fixation system of claim 16, wherein the template portion comprises a plurality of linearly arranged apertures.

* * * * *